(12) United States Patent
Dubois

(10) Patent No.: US 8,748,651 B2
(45) Date of Patent: Jun. 10, 2014

(54) METHOD FOR THE SYNTHESIS OF AN OMEGA-AMINO ACID OR ESTER STARTING FROM A MONOUNSATURATED FATTY ACID OR ESTER

(75) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 552 days.

(21) Appl. No.: 13/129,583

(22) PCT Filed: Nov. 17, 2009

(86) PCT No.: PCT/FR2009/052196
§ 371 (c)(1),
(2), (4) Date: May 17, 2011

(87) PCT Pub. No.: WO2010/055273
PCT Pub. Date: May 20, 2010

(65) Prior Publication Data
US 2011/0224454 A1      Sep. 15, 2011

(30) Foreign Application Priority Data
Nov. 17, 2008   (FR) ...................................... 08 57780

(51) Int. Cl.
*C07C 229/00*   (2006.01)
(52) U.S. Cl.
USPC ........................................................ 560/155

(58) Field of Classification Search
CPC ............................ C07C 229/08; C07C 227/04
USPC ............................................ 560/155; 553/553
See application file for complete search history.

(56) References Cited

U.S. PATENT DOCUMENTS

2009/0259065 A1*  10/2009  Abraham et al. ............. 558/340

FOREIGN PATENT DOCUMENTS

GB                741739         * 12/1955

OTHER PUBLICATIONS

Ho et al. (A Design-of-Experiments Approach for the Optimization and Understanding of the Cross-Metathesis Reaction of Methyl Ricinoleate with Methyl Acrylate, Chem Sus Chem, vol. 2, 749-754, 2009).*

* cited by examiner

*Primary Examiner* — Brandon Fetterolf
*Assistant Examiner* — Blaine G Doletski
(74) *Attorney, Agent, or Firm* — Smith, Gambrell & Russell, LLP

(57) ABSTRACT

The invention relates to a method for the synthesis of ω-amino alkanoic acids or esters thereof starting from unsaturated natural fatty acids passing through an ω-unsaturated nitrile intermediate compound.

8 Claims, No Drawings

METHOD FOR THE SYNTHESIS OF AN OMEGA-AMINO ACID OR ESTER STARTING FROM A MONOUNSATURATED FATTY ACID OR ESTER

CROSS-REFERENCE TO RELATED APPLICATIONS

This application is a national stage application under 35 U.S.C. §371 of PCT/FR2009/052196, filed Nov. 17, 2009, which claims benefit to French application FR 0857780, filed on Nov. 17, 2008, all of which are hereby incorporated by reference.

FIELD OF THE INVENTION

The invention is targeted at a process for the synthesis of ω-aminoalkanoic acids or their esters from natural unsaturated fatty acids passing through an intermediate compound of ω-unsaturated nitrile type.

BACKGROUND OF THE INVENTION

The polyamides industry uses a whole range of monomers consisting of long-chain ω-amino acids, normally known as Nylon, characterized by the length of methylene chain $(-CH_2-)_n$ separating two amide functional groups $-CO-NH-$. Thus it is that Nylon 6, Nylon 6,6, Nylon 6,10, Nylon 7, Nylon 8, Nylon 9, Nylon 11, Nylon 13, and the like, are known.

These monomers are, for example, manufactured by a chemical synthesis route using in particular, as starting material, $C_2$ to $C_4$ olefins, cycloalkanes or benzene but also castor oil (Nylon 11), erucic or lesquerolic oil (Nylon 13), and the like.

Current developments with regard to the environment are resulting in the use of natural starting materials originating from a renewal source being favored in the fields of energy and chemistry. This is the reason why some studies have been taken up to develop, industrially, processes using fatty acids/esters as starting material in the manufacture of these monomers.

This type of approach has only a few industrial examples. One of the rare examples of an industrial process using a fatty acid as starting material is that of the manufacture, from the ricinoleic acid extracted from castor oil, of 11-aminoundecanoic acid, which forms the basis of the synthesis of Rilsan 11®. This process is described in the work "Les Procédés de Pétrochimie" [Petrochemical Processes] by A. Chauvel et al., which appeared in Editions Technip (1986). 11-Aminoundecanoic acid is obtained in several stages. The first consists of a methanolysis of castor oil in a basic medium, producing methyl ricinoleate, which is subsequently subjected to a pyrolysis in order to obtain, on the one hand, heptanaldehyde and, on the other hand, methyl undecylenate. The latter is converted to the acid form by hydrolysis. Subsequently, the acid formed is subjected to a hydrobromination to give the ω-brominated acid, which is converted by amination to 11-aminoundecanoic acid.

The main studies have related to the synthesis of 9-aminononanoic acid, which is the precursor of Nylon 9, from oleic acid of natural origin.

As regards this specific monomer, mention may be made of the work "n-Nylons, Their Synthesis, Structure and Properties", 1997, published by J. Wiley and Sons, chapter 2.9 (pages 381 to 389) of which is devoted to Nylon 9. This article summarizes the preparations and studies carried out with regard to the subject. Mention is made therein, on page 381, of the process developed by the former Soviet Union which has resulted in the commercialization of Pelargon®. Mention is also made therein, on page 384, of a process developed in Japan which uses oleic acid originating from soybean oil as starting material. The corresponding description makes reference to the work by A. Ravve "Organic Chemistry of Macromolecules" (1967) Marcel Dekker, Inc., part 15 of which is devoted to polyamides and which mentions, on page 279, the existence of such a process.

In order to be fully informed with regard to the state of the art on this subject, mention should be made of the numerous papers published by E. H. Pryde et al. between 1962 and 1975 in the Journal of the American Oil Chemists' Society—"Aldehydic Materials by the Ozonization of Vegetable Oils", Vol. 39, pages 496-500; "Pilot Run, Plant Design and Cost Analysis for Reductive Ozonolysis of Methyl Soyate", Vol. 49, pages 643-648, and R. B. Perkins et al., "Nylon-9 from Unsaturated Fatty Derivatives: Preparation and Characterization", JAOCS, Vol. 52, pages 473-477. It should be noted that the first of these papers also makes reference, on page 498, to previous studies carried out by the Japanese authors H. Otsuki and H. Funahashi.

To summarize this part of the state of the art targeted at this type of synthesis of "Nylon 9" from vegetable oils, a description may be given of the following simplified reaction mechanism applied to the oleic ester extracted from the oils by methanolysis:

Reductive Ozonolysis

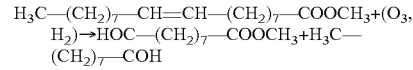

Reductive Amination

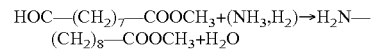

Hydrolysis

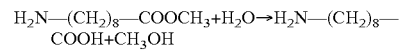

However, this route, which is very attractive from the reaction viewpoint, exhibits a significant economic drawback consisting of the production, during the first stage, of a long-chain aldehyde (9 carbon atoms in total) which is virtually nonrecoverable in value, in particular in the polymer industry relating to polyamides.

The UK patent No. 741 739 describes, for its part, the synthesis of this same acid from oleic acid but using the oleonitrile route. The simplified reaction scheme for this process is as follows. An analogous route is mentioned in the abovementioned paper by R. B. Perkins et al., p. 475.

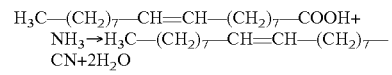

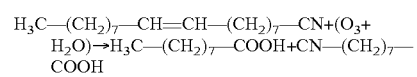

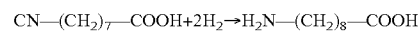

This synthesis results in pelargonic acid $H_3C-(CH_2)_7-COOH$ as byproduct.

The present invention is targeted at providing a novel process for synthesizing a whole range of ω-amino-alkanoic acids or their esters from natural unsaturated fatty acids.

The problem is thus that of finding a process for the synthesis of various ω-amino acids of formula $H_2N-(CH_2)_n-$ COOH (and of their polymers) in which n is between 3 and 14, starting from renewable starting materials (very widely accessible and therefore inexpensive), which is simple to carry out while avoiding, on the one hand, the environmental constraints mentioned above and, on the other hand, the economic handicaps due to the byproducts from the reactions.

The solution provided consists in working from starting materials consisting of natural long-chain unsaturated fatty acids, in converting them, in a first stage, into ω-unsaturated nitriles and in then subsequently, in a second stage, "reinserting" a carboxylic acid functional group into the compound by an action on the end double bond of the ω-unsaturated nitrile, either by means of oxidative cleavage or by a cross metathesis reaction with a compound of acrylate type.

DETAILED DESCRIPTION OF CERTAIN EMBODIMENTS OF THE INVENTION

The term "natural fatty acid" is understood to mean an acid resulting from the plant or animal milieu, including algae, more generally from the plant kingdom, and thus renewable. This acid will comprise at least one olefinic unsaturation, the location of which in the x position with respect to the acid group (delta x) and comprising at least 10 and preferably at least 14 carbon atoms per molecule will make it possible to determine the formula of the final ω-amino acid.

Mention may be made, as examples of such acids, of the $C_{10}$ acids obtusilic (cis-4-decanoic) acid and caproleic (cis-9-decenoic) acid, the $C_{12}$ acids lauroleic (cis-5-dedecenoic) acid and linderic (cis-4-dodecenoic) acid, the $C_{14}$ acids myristoleic (cis-9-tetradecenoic) acid, physeteric (cis-5-tetradecenoic) acid and tsuzuic (cis-4-tetradecenoic) acid, the $C_{16}$ acid palmitoleic (cis-9-hexadecenoic) acid, the $C_{18}$ acids oleic (cis-9-octadecenoic) acid, elaidic (trans-9-octa-decenoic) acid, petroselinic (cis-6-octadecenoic) acid, vaccenic (cis-11-octadecenoic) acid and ricinoleic (12-hydroxy-cis-9-octadecenoic) acid, the $C_{20}$ acids, gadoleic (cis-9-eicosenoic) acid, gondoic (cis-11-eicosenoic), cis-5-eicosenoic acid and lesquerolic (14-hydroxy-cis-11-eicosenoic) acid, and the $C_{22}$ acids cetoleic (cis-11-docosenoic) acid and eruric (cis-13-dodecosenoic) acid.

These various acids result from the vegetable oils extracted from various oleaginous plants, such as sunflower, rape, castor oil plant, bladderpod, olive, soya, palm tree, avocado, sea buckthorn, coriander, celery, dill, carrot, fennel or *Limnanthes alba* (meadowfoam).

They also result from the terrestrial or marine animal world and, in the latter case, both in the form of fish or mammals, on the one hand, and of algae, on the other hand. They are in general fats originating from ruminants, from fish, such as cod, or from marine mammals, such as whales or dolphins.

The invention is targeted at a process for the synthesis of an ω-amino acid (ester) of formula $ROOC-(CH_2)_q-CH_2NH_2$, in which R is H or an alkyl radical comprising from 1 to 4 carbon atoms and q is an integral index of between 2 and 13, starting from a monounsaturated fatty acid (ester) of formula $R_1-CH=CH-(CH_2)_p-COOR_2$, in which $R_1$ is H or a hydrocarbon radical comprising from 4 to 11 carbon atoms and, if appropriate, a hydroxyl functional group, $R_2$ is H or an alkyl radical comprising from 1 to 4 carbon atoms and p is an integral index of between 2 and 11, comprising an ammoniation reaction stage resulting in the conversion of the carbonyl functional group to a nitrile functional group, characterized in that:

in a first stage, the unsaturated fatty acid/ester is converted to an ω-unsaturated nitrile of formula $CH_2=CH-(CH_2)_p-CN$ in two successive (in any order) ethenolysis and ammoniation stages, then, in a second stage, this ω-unsaturated nitrile is converted to an acid/ester nitrile of formula $R_3OOC-[CH=CH]_x-(CH_2)_p-CN$, in which $R_3$ is H or an alkyl radical comprising from 1 to 4 carbon atoms and x is 0 or 1, either by oxidative cleavage of the ω-unsaturated nitrile or by a cross metathesis reaction of the ω-unsaturated nitrile with an acrylate of formula $CH_2=CH-COOR_3$, and, in a third stage, the acid/ester nitrile is hydrogenated to give an ω-amino acid (ester) of formula $ROOC-(CH_2)_q-CH_2NH_2$. The reaction process is then as follows.

First Stage:

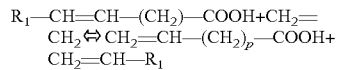

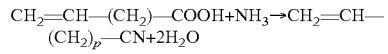

or, by reversing the order of the reactions,

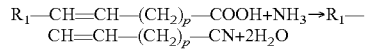

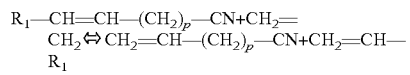

Second Stage:
  first alternative form

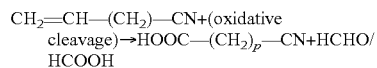

second alternative form

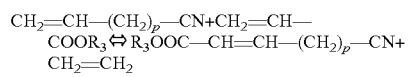

Third Stage:

first alternative form: 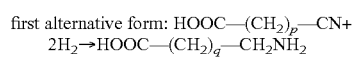

second alternative form: 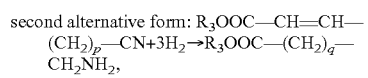

In this embodiment of the process, q is equal to p or to p+2.

Applied to oleic acid, the process becomes

First Stage:

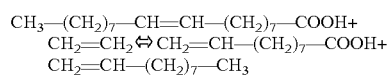

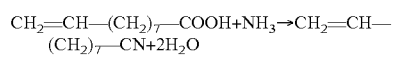

or, by reversing the order of the reactions,

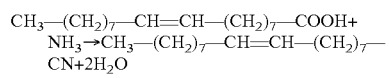

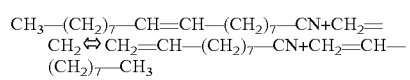

Second Stage:
  first alternative form

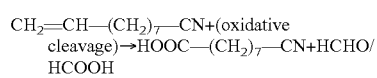

second alternative form

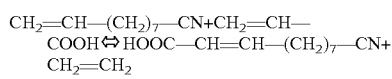

Third Stage:

first alternative form: $HOOC-(CH_2)_7-CN + 2H_2 \rightarrow HOOC-(CH_2)_7-CH_2NH_2$ second alternative form: $HOOC-CH=CH-(CH_2)_7-CN + 3H_2 \rightarrow HOOC-(CH_2)_9-CH_2NH_2$ The only "byproducts" formed are a long-chain α-olefin, if appropriate comprising a hydroxyl functional group, and formaldehyde/formic acid.

In a simplified alternative embodiment of the process of the invention, it is possible to save a stage by synthesizing, during the first stage, the nitrile of the fatty acid/ester of formula $R_1-CH=CH-(CH_2)_p-CN$ by ammoniation of the starting acid/ester and by then subjecting the latter to a cross metathesis with an acrylate $R_3OOC-CH=CH_2$, in order to obtain the acid nitrile of formula $R_3OOC-CH=CH-(CH_2)_p-CN$, which will subsequently be hydrogenated to give $R_3OOC-(CH_2)_{p+2}-CH_2NH_2$.

In another alternative form of the process in which hydroxylated fatty acids, such as ricinoleic acid and lesquerolic acid, which correspond to the general formula $R_1-CH=CH-(CH_2)_p-COOH$ with $R_1$ equal to $CH_3-(CH_2)_5CHOH-CH_2-$ and p equal to 7 and 9 respectively, are used as starting material, the acid in its methyl ester form is subjected to a pyrolysis resulting in an ω-unsaturated ester of formula $CH_2=CH-(CH_2)_{p+1}-COOCH_3$, which is converted, directly or by passing through the acid, to an ω-unsaturated nitrile of the same nature as that of the intermediate compound obtained on completion of the first stage of the process described above. This alternative form thus consists in replacing, for these specific fatty acids, the initial ethenolysis by a pyrolysis.

The following stages of the process are analogous to those of the process described above. They thus result in compounds of formula $ROOC-(CH_2)_q-CH_2NH_2$ in which q is equal to p+1 or to p+3, according to the route selected during the second stage.

Thus, in preferred embodiments of the invention:
- during the first stage, the ethenolysis of the acid (ester) is first of all carried out, to be followed by the ammoniation of the ω-alkenoic acid;
- during the first stage, the ammoniation of the acid (ester) is first of all carried out, to be followed by the ethenolysis of the nitrile of the starting fatty acid;
- during the first stage, the pyrolysis of the hydroxylated fatty acid (ester) is first of all carried out, to be followed by the ammoniation of the ω-alkenoic acid (ester) resulting from the pyrolysis;
- during the first stage, the ammoniation of the acid (ester) is carried out, without proceeding to the ethenolysis reaction;
- during the second stage, the ω-unsaturated nitrile of formula $CH_2=CH-(CH_2)_p-CN$ is subjected to an oxidative cleavage;
- during the second stage, the product resulting from the first stage is subjected to a cross metathesis reaction with the compound of acrylate type; and/or
- the compound resulting from the second stage is subjected to a hydrogenation.

The metathesis reactions have been known for a long time, even if their industrial applications are relatively limited. Reference may be made, with regard to their use in the conversion of fatty acids (esters), to the paper by J. C. Mol, "Catalytic Metathesis of Unsaturated Fatty Acid Esters and Oil", which appeared in Tropics in Catalysis, Vol. 27, Nos. 1-4, February 2004 (Plenum Publishing).

The catalysis of the metathesis reaction has formed the subject of a great many studies and the development of sophisticated catalytic systems. Mention may be made, for example, of the tungsten complexes developed by Schrock et al., J. Am. Chem. Soc., 108 (1986), 2771, or Basset et al., Angew. Chem., Ed. Engl., 31 (1992), 628. More recently, "Grubbs" catalysts, which are ruthenium-benzylidene complexes, have appeared (Grubbs et al., Angew. Chem., Ed. Engl., 34 (1995), 2039, and Organic Lett., 1 (1999), 953). These relate to homogeneous catalysis. Heterogeneous catalysts have also been developed which are based on metals, such as rhenium, molybdenum and tungsten, deposited on alumina or silica.

Finally, studies have been carried out on the preparation of immobilized catalysts, that is to say catalysts whose active principle is that of a homogeneous catalyst, in particular ruthenium-carbene complexes, but which is immobilized on an inactive support. The object of these studies is to increase the selectivity of the cross metathesis reaction with regard to the side reactions, such as "homometathesis" between the reactants brought together. They relate not only to the structure of the catalysts but also to the effect of the reaction medium and the additives which may be introduced.

Any active and selective metathesis catalyst can be used in the process of the invention. However, use will preferably be made of ruthenium-based catalysts.

The cross metathesis reaction with ethylene during one of the stages of the first phase is carried out at a temperature of between 20 and 100° C. at a pressure of 1 to 30 bar in the presence of a conventional metathesis catalyst, for example of ruthenium type. The reaction time is chosen according to the reactants employed and in order to reach as close as possible to the equilibrium of the reaction. The reaction is carried out under an ethylene pressure.

The cross metathesis reaction with the compound of acrylate type is carried out under conditions which are fully known. The reaction temperature is between 20 and 100° C., generally at atmospheric pressure, in order to make possible ready release of the ethylene, in the presence of a ruthenium-based catalyst.

The ruthenium catalysts are preferably chosen from the charged or uncharged catalysts of general formula:

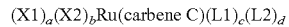

in which;
- a, b, c and d are integers with a and b equal to 0, 1 or 2 and c and d equal to 0, 1, 2, 3 or 4;
- X1 and X2, which are identical or different, each represent a charged or uncharged and mono- or multichelating ligand; mention may be made, by way of examples, of halides, sulfate, carbonate, carboxylates, alkoxides, phenolates, amides, tosylate, hexafluoro-phosphate, tetrafluoroborate, bistriflylamide, tetra-phenylborate and derivatives. X1 or X2 can be bonded to Y1 or Y2 or to the (carbene C) so as to form a bidentate ligand (or chelate) on the ruthenium; and
- L1 and L2, which are identical or different, are electron-donating ligands, such as phosphine, phosphite, phosphonite, phosphinite, arsine, stilbene, an olefin or an aromatic, a carbonyl compound, an ether, an alcohol, an amine, a pyridine or a derivative, an imine, a thioether or a heterocyclic carbene, L1 or L2 can be bonded to the "carbene C" so as to form a bidentate ligand or chelate, The "carbene C" can be represented by the general formula: $C_-(R1)_-(R2)$ for which R1 and R2 are identical or different, such as hydrogen or any other saturated or unsaturated, cyclic, branched or linear, or aromatic hydrocarbonyl group. Mention may be made, by way of examples, of alkylidene or cumulene complexes of ruthenium, such as vinylidenes Ru=C=CHR or allenylidenes Ru=C=C=CR1R2 or indenylidenes.

A functional group which makes it possible to improve the retention of the ruthenium complex in the ionic liquid can be grafted to at least one of the ligands X1, X2, L1 or L2 or to the carbene C. This functional group can be charged or uncharged, such as, preferably, an ester, an ether, a thiol, an acid, an alcohol, an amine, a nitrogenous heterocycle, a sulfonate, a carboxylate, a quaternary ammonium, a guanidinium, a quaternary phosphonium, a pyridinium, an imidazolium, a morpholinium or a sulfonium.

The reaction scheme for the synthesis of the nitriles starting from the acids, which is well known to a person skilled in the art, can be summarized in the following way:

R—COOH+NH$_3$→[R—COO$^-$NH$_4^+$]→[R—CONH$_2$]+H$_2$O→RCN+H$_2$O

This scheme applies equally well to the natural fatty acids (esters) as to the ω-unsaturated fatty acids.

The process can be carried out batchwise in the liquid or gas phase or continuously in the gas phase. The reaction is carried out at a high temperature>250° C. and in the presence of a catalyst which is generally a metal oxide and more frequently zinc oxide. The continuous removal of the water formed while moreover entraining the unreacted ammonia makes possible rapid completion of the reaction.

The pyrolysis reaction employed in the alternative form of the process is carried out on the ester form of the hydroxylated fatty acid concerned, generally the methyl ester. The reaction is carried out at high temperature, of between 400 and 750° C. and preferably between 500 and 600° C., in the presence of superheated steam.

The pyrolysis reaction applied to methyl ricinoleate corresponds to the following process:

CH$_3$—(CH$_2$)$_5$CHOH—CH$_2$—CH=CH—(CH$_2$)$_7$—COOCH$_3$+Δ→CH$_3$—(CH$_2$)$_5$CHO+CH$_2$=CH—(CH$_2$)$_7$—COOCH$_3$

It is followed by an ammoniation:

CH$_2$=CH—(CH$_2$)$_7$—COOCH$_3$+NH$_3$→CH$_2$=CH—(CH$_2$)$_7$—CN+2H$_2$O.

The stage of synthesis of the fatty ω-amino acids (esters) from the fatty acid nitriles consists of a conventional hydrogenation. There are many catalysts but use is preferably made of Raney nickels and cobalts. In order to promote the formation of the primary amine, the hydrogenation is carried out with an ammonia partial pressure. Finally, the reduction of the nitrile functional group to give a primary amine is well known to a person skilled in the art.

The oxidative cleavage reaction on the double bond, which results in the formation of the acid functional group on the two carbons of the double bond, is also known per se. It can be carried out using a wide range of strong oxidizing agents.

For example, it can be carried out by means of a strong oxidizing agent, such as KMnO$_4$ in the concentrated form and with heating, as is described in "Organic Chemistry" by L. G. Wade Jr., 5$^{th}$ edition, Chapter 8, Reactions of Alkenes.

The oxidative cleavage can be obtained by a route involving a sulfuric acid/chromic acid mixture, such as described in the U.S. Pat. No. 2,871,247, in columns 2 and 3.

Moreover, the paper by G. S. Zhang et al. in Chinese Chemical Letters, Vol. 5, No. 2, pp. 105-108, 1994, indicates that it is possible to carry out the oxidative cleavage starting from the corresponding diol of oleic acid (see Entry 29 of the table). This oxidative cleavage is carried out using ammonium chlorochromate as oxidizing agent. For its part, the diol is obtained by epoxidation of oleic acid, followed by hydrolysis of the epoxy bridge.

The paper by F. Drawert et al. in Chem. Mikrobiol. Technol. Lebensm., 1, 158-159 (1972), describes an alternative route by irradiation of sunflower oil.

The oxidative cleavage can be carried out with aqueous hydrogen peroxide solution, as described in the patent GB 743 491. The use of H$_2$O$_2$ is also described in the patent WO07039481 (Novamont).

Mention may also be made of the work Angew. Chem. Int. Ed., 2000, 39, pp. 2206-2224, which describes the oxidative cleavage of the double bond, either, on the one hand, with a peracid in combination with a ruthenium-based catalyst or, on the other hand, with H$_2$O$_2$ with catalysts based on Mo, W or Re.

Numerous studies have been carried out on the use of ozone as oxidizing agent. Furthermore, it is mentioned, in the abovementioned Angew. Chem. work, that the oxidative cleavage of oleic acid to perlargonic acid and azelaic acid is the most important industrial application of ozonolysis.

The U.S. Pat. No. 2,813,113 describes in particular a process for the oxidative ozonolysis of a fatty acid, such as oleic acid, which consists, in a first stage, in treating the acid with oxygen in combination with ozone, in order to form ozonides, and then, in a second stage, in oxidizing the latter compounds with oxygen.

Use is not made, in this type of reaction, of compounds which block the oxidation process at the stage of the ketones or aldehydes, in what is known as reductive ozonolysis, which has more recently formed the subject of important studies.

In the process of the invention, the fatty acid can be treated either in its acid form or in its ester form. The perfectly commonplace change from one form to the other, by methanolysis, esterification or hydrolysis, does not constitute a chemical conversion within the meaning of the process.

All the mechanisms described below illustrate, in order to facilitate the account, the synthesis of the acids. However, the metathesis is also effective with an ester and even more effective, the medium generally being more anhydrous. In the same way, the schemes illustrate reactions with the cis isomer of the acids (or esters); the mechanisms are applicable equally well to the trans isomers.

The reaction mechanism of this reaction is illustrated in scheme 1 below.

Scheme 1

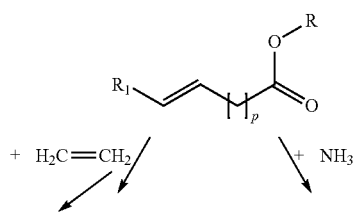

-continued
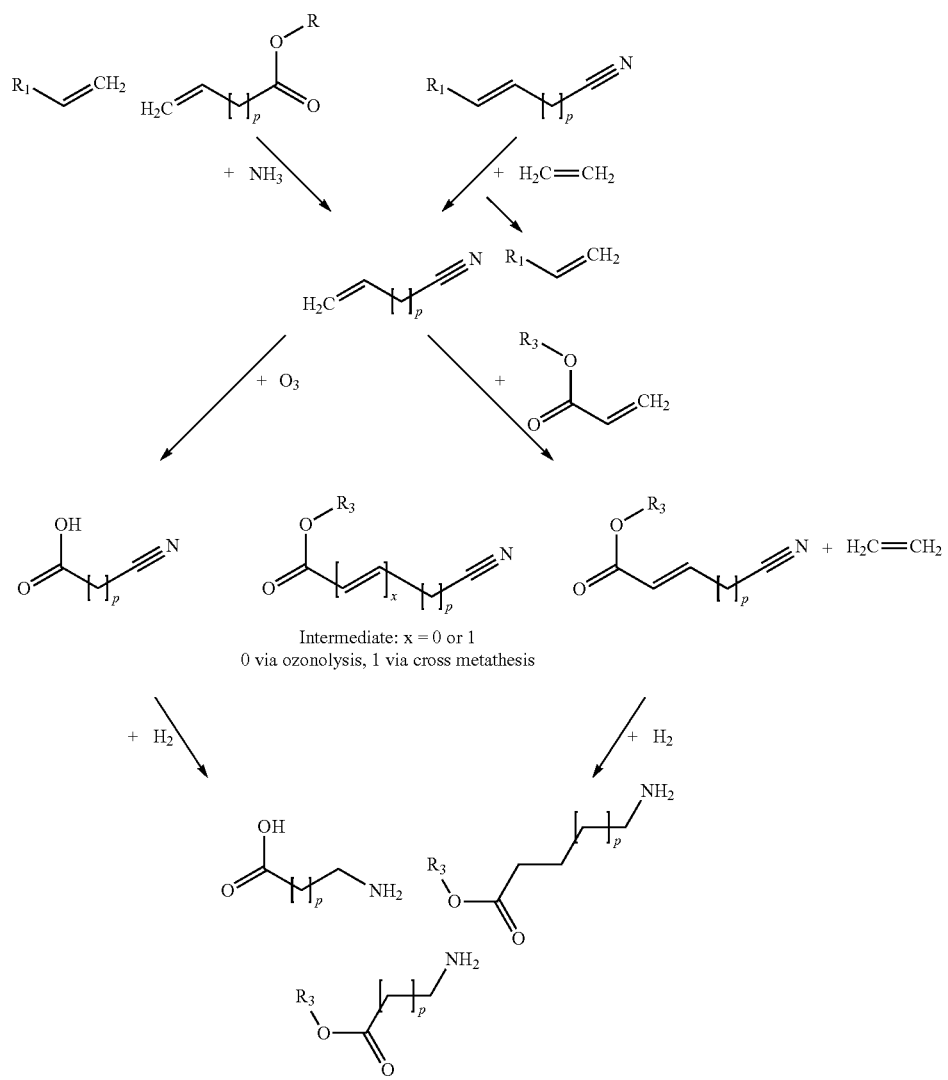
(in the above scheme, q=p according to the ozonolysis route and q=p+2 according to the cross metathesis route)
The alternative embodiment of the process of the invention applied to hydroxylated unsaturated fatty acids is illustrated by scheme 2 below.
Scheme 2
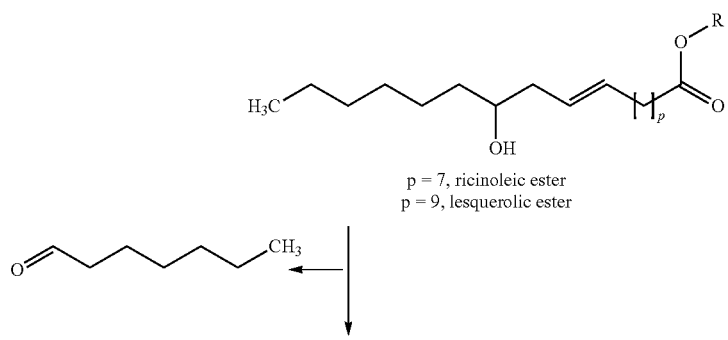
p = 7, ricinoleic ester
p = 9, lesquerolic ester

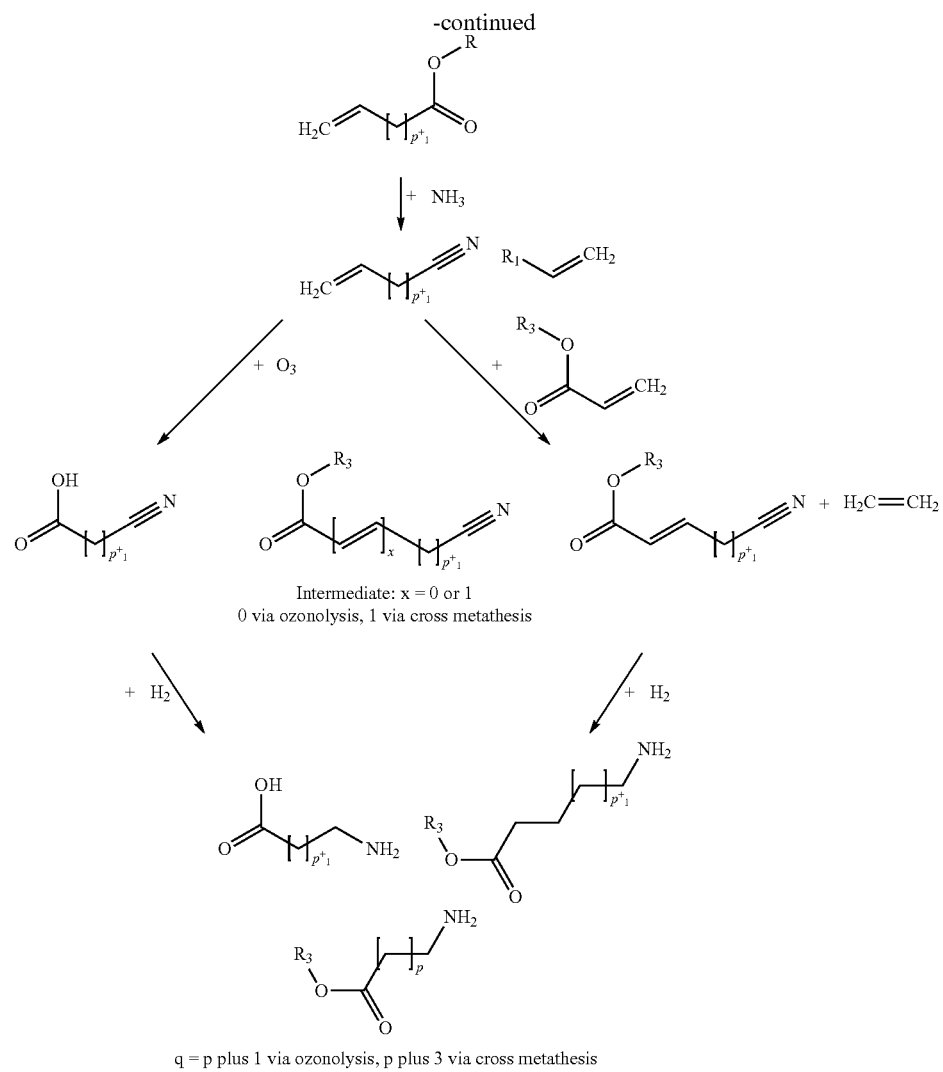

q = p plus 1 via ozonolysis, p plus 3 via cross metathesis

The invention additionally relates to the amino acid or amino ester of renewable origin of general formula $NH_2CH_2-(CH_2)_q-COOR$, R being either H or an alkyl radical comprising from 1 to 4 carbon atoms.

The term "amino acids or amino esters of renewable origin" is understood to mean the amino acids or amino esters which comprise carbon of renewable origin.

By employing the process of the invention, it will be possible to synthesize a whole range of ω-amino acids.

4-Aminotetranoic acid is obtained from obtusilic, linderic and tsuzuic acids.

5-Aminopentanoic acid is obtained from lauroleic, physeteric and cis-5-eicosenoic acids.

6-Aminohexanoic acid is obtained from obtusilic, linderic, tsuzuic and petroselenic acids.

7-Aminoheptanoic acid is obtained from lauroleic, physeteric and cis-5-eicosenoic acids.

8-Aminooctanoic acid is obtained from petroselenic acid.

9-Aminononanoic acid is obtained from caproleic, myristoleic, palmitoleic, oleic, elaidic, ricinoleic and gadoleic acids.

10-Aminodecylenic acid is obtained from ricinoleic acid.

11-Aminoundecylenic acid is obtained from caproleic, myristoleic, palmitoleic, oleic, elaidic, ricinoleic, gadoleic, vaccenic, gondoic, lesquerolic and cetoleic acids.

12-Aminododecylenic acid is obtained from ricinoleic and lesquerolic acids.

13-Aminotridecylenic acid is obtained from vaccenic, gondoic, cetoleic, lesquerolic and erucic acids.

14-Aminotetradeylenic acid is obtained from lesquerolic acid.

15-Aminopentadecylenic acid is obtained from erucic acid.

The invention is illustrated by the following examples.

EXAMPLE 1

This example illustrates the first stage of ethenolysis of methyl oleate according to the process which is a subject matter of the invention. Use is made, for this reaction, of the complex catalyst $[RuCl_2(=CHPh)(IMesH_2)(PCy_3)]$, the formula (A) of which is given below. The reaction is carried out in $CH_2Cl_2$, at a methyl oleate concentration of 0.05M and an ethylene concentration of 0.2M, at a temperature of 55° C., at atmospheric pressure, for 6 hours, in the presence of the catalyst at a concentration of 5 mol %, with respect to the methyl oleate. The yields are determined by chromatographic analysis. A yield of methyl 9-decenoate $CH_2=CH-(CH_2)_7-COOCH_3$ and of 1-decene of 55 mol % can be measured.

Catalyst of Formula (A)

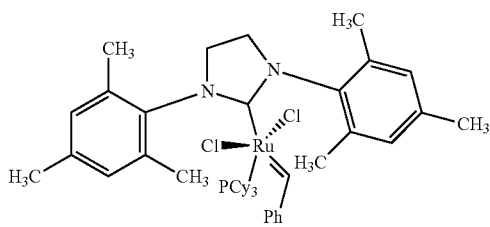

EXAMPLE 2

This example illustrates the second stage of ammoniation in which 9-decenoic acid, resulting after hydrolysis of the ester of the first stage, is converted to the nitrile of formula CN—(CH$_2$)$_7$—CH═CH$_2$.

The ammoniation reaction of 9-decenoic acid (3.5 g) to form the ω-unsaturated nitrile of formula CN—(CH$_2$)$_7$—CH═CH$_2$ is carried out batchwise with introduction of ammonia in molar excess with respect to the acid and at a temperature of 300° C. at atmospheric pressure (in the gas phase) in the presence of a zinc oxide catalyst. The reactor is equipped with a condenser at 100° C. Ammonia is also continuously injected for 6 hours. The continuous removal of the water formed entrains the excess ammonia and makes possible rapid completion of the reaction. 2.6 g of the nitrile are recovered and are separated by vacuum distillation.

EXAMPLE 3

This example illustrates the oxidative cleavage of the ω-unsaturated nitrile resulting from the stage of example 2 by ozonolysis to form the acid nitrile of formula CN—(CH$_2$)$_7$—COOH.

Ozone obtained by a Welsbach T-408 ozone generator is bubbled into 25 ml of pentane until a blue color is observed. The pentane solution is kept at −70° C. with an acetone/dry ice bath. 20 mg of methyl ester of a nitrile obtained in accordance with example 2, dissolved in 5 ml of pentane cooled to 0° C., are added to the ozone solution. The excess ozone is subsequently removed and the blue color disappears. After 5 minutes, the pentane is evaporated with a stream of dry nitrogen. During this stage, the temperature of the solution is kept below 0° C. After evaporating the pentane, 3 ml of methanol cooled to −70° C. are added to the reactor while reheating it in order to make possible the dissolution of the ozonide. In order to carry out the conversion of the ozonide to the acid nitrile, the temperature is first raised to approximately 60° C. When the reaction for the decomposition of the ozonide begins, it is accompanied by a rise in the temperature. A stream of oxygen is continuously added, in order to maintain the temperature and to directly oxidize the products resulting from the decomposition of the ozonide. The procedure is carried out over 4 hours in order to limit the formation of decomposition products. It is important to maintain the reaction temperature slightly above the decomposition temperature of the ozonide during this stage. A temperature of 95° C. is used in this example.

6 mg of acid nitrile of formula CN—(CH$_2$)$_7$—COOH are obtained.

EXAMPLE 3a

This example illustrates an alternative form of oxidative cleavage of the ω-unsaturated nitrile.

50 g of an unsaturated nitrile synthesized in accordance with example 2 are ozonized at −40° C. in ethyl chloride using oxygen comprising 3.7% of ozone. The solvent is subsequently distilled off and the ozonide is treated under reflux for 30 minutes with 100 g of water. The mixture is subsequently cooled, excess sodium carbonate is added and the mixture is stirred at 40° C. for 10 minutes. The undissolved fraction is separated and removed. The soluble fraction is acidified with 10% hydrochloric acid and the acids are separated and dried over magnesium sulfate. The mixture of aldehydes is oxidized with molecular oxygen at 120-140° C. for 1 hour in the presence of ferric oxide. The acids are extracted with a sodium carbonate solution and liberated with a hydrochloric solution, separated and dried over anhydrous magnesium sulfate. The two batches of acids are combined and distilled under vacuum at 196° C. (5 mmHg).

15 g of acid nitrile are dissolved in 160 g of ethanol and 15 g of liquid ammonia. The solution is placed in a stirred autoclave with 3 g of Raney nickel catalyst and under a pressure of 110 bar of hydrogen. The temperature is raised to 100° C. and the pressure increases up to 139 bar. The conditions are maintained for 4 hours. The autoclave is cooled and the contents are filtered in order to recover the catalyst. 50 g of water are then added and the alcohol is distilled off. The resulting solution is titrated with dilute hydrochloric acid and the aminononanoic acid is filtered off, washed and treated under reflux of acetone, and dried.

EXAMPLE 4

This example illustrates the cross metathesis reaction between a nitrile of formula CN—(CH$_2$)$_7$—CH═CH$_2$, resulting from the stage of example 2, with methyl acrylate according to the reaction:

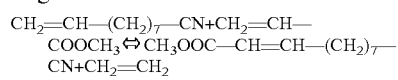

83 mg of 9-cyanoundecene (0.5 mmol), 86 mg of methyl acrylate (1 mmol) and 10 ml of toluene distilled over sodium/benzophenone are charged to a 50 ml Schlenk tube. 1.5 mg (2.4×10$^{-3}$ mmol) of Hoveyda-Grubbs catalyst, second generation, [(1,3-bis(2,4,6-trimethyl-phenyl)-2-imidazolidinylidene)dichloro(o-isopropoxy-phenylmethylene]ruthenium, sold by Aldrich®, are added. Heating is carried out to 100° C. and reaction is allowed to take place for 1 hour, under nitrogen and with magnetic stirring. The reaction mixture is analyzed by gas chromatography (dodecane standard). The conversion is 70%. The selectivity for methyl ester nitrile (cis+trans mixture) is 100%.

EXAMPLE 5

This example illustrates the alternative form with inversion of the order of the 2 stages of phase 1: ammoniation of the unsaturated fatty acid, followed by ethenolysis of the unsaturated nitrile.

The ammoniation of oleic acid is carried out batchwise with introduction of ammonia in molar excess with respect to the acid and at a temperature of 300° C. at atmospheric pressure (in the gas phase) in the presence of a zinc oxide catalyst. The continuous removal of the water formed entrains the excess of ammonia and makes possible rapid completion of the reaction.

The ethenolysis of the nitrile of oleic acid is carried out at 60° C. at atmospheric pressure in the presence of a ruthenium-based catalyst [RuCl$_2$(═CHPh)(IMesH$_2$)(PCy$_3$)] while using an excess of ethylene, in order to obtain 9-decenoic acid $CH_2$=CH—$(CH_2)_7$—COOH. The yields are determined by chromatographic analysis. On completion of the reaction, 6 hours, the $C_{10}$ α-olefin is separated by vacuum distillation in order to obtain the 9-decenoic nitrile $CH_2$=CH—$(CH_2)_7$—CN. The yields are determined by chromatographic analysis. A yield of 55% can be measured.

EXAMPLE 6

Pyrolysis of Hydroxylated Fatty Acid

The triglyceride of ricinoleic acid is transesterified with an excess of methanol in the presence of sodium methoxide.

The ester is then vaporized at 225° C. and subsequently mixed with superheated steam (620° C.) The reaction is short, approximately 10 seconds. The methyl undecenoate is subsequently purified, first of all by cooling the medium, which makes possible the extraction of the water, and then by a series of distillations which make possible the separation of the ester and reaction byproducts.

EXAMPLE 7

Hydrogenation

The hydrogenation of the double bond and of the nitrile functional group is carried in the presence of a catalyst composed of a Raney nickel.

1 g of acid nitrile of formula CN—$(CH_2)_7$—COOH obtained in accordance with example 3 is esterified with methanol. 1 g of acid nitrile, 1.2 g of methanol, 1.2 g of benzene and a few drops of concentrated sulfuric acid are introduced into a reactor. The water/alcohol/benzene azeotrope is removed at the column top. Sulfuric acid is added continuously in order to keep the reaction progressing. Subsequently, the benzene and alcohol are flash distilled in order to recover the ester nitrile: 1.02 g.

The ester nitrile synthesized is placed in a stirred 15 ml autoclave and 2.5 g of 96% ethanol, 2.5 g of liquid ammonia and 0.125 g of Raney nickel catalyst comprising 3% by weight of cobalt are added thereto.

The mixture is heated at 90° C. for 4 hours under 150 bar hydrogen (total pressure 210 bar). The methyl ester is distilled under a vacuum of 0.5 mm of mercury. 0.97 g of a clear distillate is recovered. It comprises 90% of amino ester.

EXAMPLE 8

The amino acid is intended to be polymerized. For this, the amino ester is hydrolyzed. The methyl 9-amino-nonanoate obtained is placed in a dropping funnel in order to be run dropwise into a 2 liter three-necked round-bottomed flask surmounted by a long distillation column and comprising one liter of refluxing water. Reflux is regulated so as to distill off the methanol formed, which makes it possible to monitor the reaction; the hydrolysis lasts from 4 to 5 hours for the methyl ester. When the reaction is complete, filtration is carried out under hot conditions and the water is evaporated. A product is obtained which is difficult to dry in a desiccator, whereas, on washing the wet product with acetone and on drying it in a desiccator, 20 g of crude colorless amino acid are collected.

What is claimed is:

1. A process for the synthesis of an ω-amino acid or ester of formula ROOC—$(CH_2)_q$—$CH_2NH_2$, in which R is H or an alkyl radical having from 1 to 4 carbon atoms and q is an integer between 2 and 13, comprising the steps of:
    a) converting a monounsaturated fatty acid or ester of formula $R_1$—CH=CH—$(CH_2)_p$—$COOR_2$ into an ω-unsaturated nitrile of formula $CH_2$=CH—$(CH_2)_p$—CN, wherein the converting step comprises in successive and in any order an ammoniation reaction and an ethenolysis reaction, wherein $R_1$ is H, or a hydrocarbon radical comprising from 4 to 11 carbon atoms which may be optionally substituted with a hydroxyl functional group, $R_2$ is H or an alkyl radical comprising from 2 to 4 carbon atoms and p is an integer between 2 and 11;
    b) converting the ω-unsaturated nitrile into an acid or ester nitrile of formula $R_3OOC$—$[CH$=$CH]_x$—$(CH_2)_p$—CN, either by oxidative cleavage of the ω-unsaturated nitrile or by a cross metathesis reaction of the co-unsaturated nitrile with an acrylate of formula $CH_2$=CH—$COOR_3$, wherein $R_3$ is H or an alkyl radical comprising from 1 to 4 carbon atoms and x is 0 or 1; and
    c) hydrogenating the acid or ester nitrile to form the co-amino acid or ester of formula ROOC—$(CH_2)_q$—$CH_2NH_2$.

2. The process of claim 1, wherein during step a), the ethenolysis of the fatty acid or ester is carried out to form a ω-alkenoic acid, followed by ammoniation of the ω-alkenoic acid.

3. The process of claim 1, wherein during step a), the ammoniation of the fatty acid or ester is carried out, followed by ethenolysis of the nitrile of the starting fatty acid or ester.

4. The process of claim 1, wherein the ethenolysis of step a) is replaced with a pyrolysis reaction of a hydroxylated fatty acid or ester to form a ω-alkenoic acid or ester followed by ammoniation of the ω-alkenoic acid or ester.

5. The process of claim 1, wherein during step b), the co-unsaturated nitrile of formula $CH_2$=CH—$(CH_2)_p$—CN is subjected to an oxidative cleavage.

6. The process of claim 1, wherein during step b), the product resulting from step a) is subjected to a cross metathesis reaction with the acrylate of formula $CH_2$=CH—$COOR_3$.

7. The chemical equation "$R_1$—$CH_2$=CH—$(CH_2)_p$—CN" is deleted and the chemical equation is put in its place "$R_1$—CH=CH—$(CH_2)_p$—CN".

8. The process of claim 7, wherein step a) further comprises pyrolysis of a hydroxylated fatty acid or ester to form a ω-alkenoic acid or ester followed by ammoniation of the ω-alkenoic acid or ester.

* * * * *